US00PP08730P

United States Patent [19]

Smith

[11] Patent Number: Plant 8,730

[45] Date of Patent: May 17, 1994

[54] ELM TREE VARIETY NAMED WIDELEAF

[76] Inventor: Raymond H. Smith, Elmsagain Nursery, 961 Bulter Ave., P.O. Box 83, Winnebago, Wis. 54985-0083

[21] Appl. No.: 35,269

[22] Filed: Mar. 22, 1993

[51] Int. Cl.[5] ..... A01H 5/00

[52] U.S. Cl. ..... Plt./53.3

[58] Field of Search ..... Plt. 53.3

[56] References Cited

PUBLICATIONS

Wyman, D., "Ulmus" *Trees for American Gardens*, Macmillan Pub. Co., N.Y., 1974, pp. 461–473.

*Primary Examiner*—James R. Feyrer

[57] ABSTRACT

A new and distinct hybrid elm selection, believed to be from a genetic background of *Ulmus americana* × *U. pumila*, which is characterized by extremely high vigor as compared to other elm trees of the same age. This tree is further characterized by having leaves which are larger, thicker, highly doubly serrate, and more symmetrical than those of comparison trees of comparison or parental species. The leaves of this tree have midrib and veins which are inserted below the top surface and protrude from the bottom surfaces of leaves, and are larger than those of other species.

It seems the extra thickness of the upper surface of the leaves of this tree with the larger vein structure beneath causes the leaf surface to become curved in a retrorse curve, with the center portion of the blade being higher, and the outer portion curved slightly downward. The blade turned with the lower side up becomes dish shaped and will hold water in the center. As the leaf matures, it take on various shaped curves over the veins outward from the center, which, as the leaf hardens in late summer, become a wavy fringe along the side.

2 Drawing Sheets

BACKGROUND OF THE INVENTION

The present invention relates to a new and distinct variety of Elm tree which is believed to be a third generation tree resulting from the interspecific hybridization of *Ulmus americana* × *U. pumila*. The tree of this invention is also believed to be the result of a series of natural pollination back crosses of the initial hybrid with either American Elm or other hybrid trees with the same genetic background, due to the numerous characteristics of this tree which characterize American Elm, yet differing in a number of respects, such as having an unusually high level of vigor and by producing leaves which are much larger than those of either *U. americana* or *U. pumila*. This tree produces leaves which are most similar to those of the American Elm, but differ slightly in terms of shape and length of leaf stem; the leaves of this tree being nearly symmetrical and having uncharacteristically short petioles. The veins of the leaves of this tree are inserted from the top surface and protrude from the bottom leaf surface to a higher degree than is characteristic for American Elm, and venation is inconspicuous from the top, but very conspicuous from the bottom surfaces of the leaves, which are also thicker than is characteristic of those of the American ancestor species. While this selection has not been systematically tested for a long period of time, its characteristics which would qualify it is useful to both the landscape artisan and a farmer wishing to grow a living windbreak. Due to the age, size and character of its known seed parent, it is believed that this tree will be unusually tolerant of, or resistant to, common diseases which discourage the planting of trees within the family Ulmaceae.

Testing for Disease Resistance

Testing was done by obtaining leaf and stem material from an American Elm dying of Dutch Elm disease and grinding it to a pulp, and on Jul. 20, 1991 inoculating each of 20 third generation elms which were 5 to 6 feet high by making a one-inch incision through the bark, prying the bark back slightly and inserting the pulp, pressing more on the outside and wrapping the whole with masking tape. From this they showed no signs of wilting, and I repeated the inoculation the next year in July of 1992 on all 20 trees in the same manner, and also as a check I inoculated 8 American Elm in a nearly lot, leaving four that were not inoculated. The 20 of this third generation of trees show no sign of disease, while all eight of the American Elm trees are dead or dying of it, and the four trees that were not inoculated show no signs of disease yet.

DESCRIPTION OF RELATED ART

This tree was a seedling selected from among the progeny of a mature Elm tree which bore characteristics of both *U. americana* and *U. pumila*, and which showed unusual resistance to common elm diseases, had an attractive upright habit, unusually ascending branch attitude and a straight, long, stately bole. This tree was believed to have been a second generation open pollinated seedling of the two species named above. A planting of seeds collected from the parent tree was made by me to form a nursery from which superior trees could be selected. This tree was selected as being exceptional within the population due to its high vigor which resulted in growth rate and size attainment of nearly twice that of the siblings at the time of selection, and because of the unusual, desirable characteristics of its leaves as noted above. I have asexually reproduced this tree by layered cuttings in the yard of my nursery in Winnebago, Wis. Clones of this tree are substantially identical to the original selection in all distinguishing characteristics, which have been reliably expressed in clonal material to demonstrate that the tree is stable.

Seed History

The type of seed from this strain of trees remained the same as the first seed gathered from the *pumila* seed-producing parent and that gathered and planted from the two succeeding generations of hybrids. The last seed gathered produced the trees from which the one for patent was selected. The parent tree has characteristics that are indistinguishable from the American Elm except for its resistance to Dutch Elm wilt, and producing seed with the *pumila* characteristics, which are a cilia-fringed, flattened, winged samara about ½ inch in diameter, light tan or cream color with a slightly darker nutlet at the center, suborbicular or nearly round in shape. In contrast, the American Elm has a samara about ½ inch long, elliptic-ovate, light brown ciliate fringe with a darker brown nutlet bordering a deep notch in the base. Parent trees flowered May 20, leaved Jun. 1, and dropped seed Jun. 10.

FIELD OF INVENTION

1905 Parent

*Ulmus americana,* L. or American Elm

Many mature 100 ft. trees, pollen producers. Description: Tall wide-spreading tree to 120 ft. much planted for avenues; bark gray and flaky; branchlets pubescent when young; leaves ovate-oblong, 3–6 in. long, abruptly acuminate, unequal at base, double serrate, almost glabrous and rough above, pubescent or almost glabrous beneath; flowers long-pedicelled, in drooping many-flowered clusters; stamens 7–8, with bright red anthers, exserted; samara about ½ in. long, retriculate-veined, glabrous, the margins densely ciliate, wings deeply notched.

1905 Parent

*Ulmus pumila,* L. or Siberian Elm

One surviving tree maturing to seed production 1925. This was an experimental tree sent by government to Nursery for testing, called Chinensis, or Chinese Elm, and was tested, grown, propagated, and sold as that. Description: Tree to 75 ft. or sometimes shrubby; branchlets soon glabrous; leaves elliptic to oblong-lanceolate, ¾ to 2½ in. long, short-acuminate, subequal at base, almost simply serrate, smooth above, glaborous to somewhat pubescent in axils of veins beneath; samara suborbicular, about ½ in. long. Siberia to Turkestan.

1925 1st Generation

From seedlings of the parent seed producing Siberian Elm 200 or more trees were transplanted from the most vigorous in growth of the seedlings and sold as Chinese Elms. A small percent (20%) of 100 seeds had about half American characteristics and one-half Siberian. The remaining 80% were Siberian in appearance.

1945 2nd Generation

1st generation Hybrid Siberian tree surrounded by mature native American trees produced seed from which 400 to 500 selected trees were transplanted and sold as Chinese/American Elms. Of these trees, 25% were all American in appearance; and the rest were half American and half Siberian in appearance. Those of Siberian appearance were eliminated in transplanting.

1990 3rd Generation

Ulmus Wideleaf

Gray flaky bark on older wood. Fast-growing branches of new growth, a smooth dark reddish brown, rougher with age, thin light gray lines later in the season, lightly lenticeled. Leaves are lanceolate, and wider than one-half their length, which is 5"–10" long. Acuminate tip, with double serrate edge, unequal base. Petiole less than ¼ in. to close. Leaf glabrous above and glaborate on midrib and veins below. Leaf larger than parent varieties.

SUMMARY OF THE INVENTION

The tree of this invention is particularly distinguished by the following characteristics which, in combination, distinguish the tree from other trees of the elm family:

1. An uncommonly high level of vigor which typically results in about twice the amount of terminal growth of other similar seedlings at early growth stages.

2. Unique, and attractive foliage: leaves of more symmetrical shape than siblings of the selection and of other trees having similar genetic background: attractive deep green coloration, very short leaf stems, greater thickness, and much larger size when compared to other leaves of seedlings of apparent similar genetic background, and of seedlings of *U. americana* and *U. pumila,* per se.

3. The branching of this tree occurred normally, the only trimming being removal of lower side branches and cutting back upper new growth about half-way for propagating material. This 1993 growing season produced a central stem of 8½ feet of new growth upward from the center of the trunk, with five stems 3 to 6 feet evenly spaced around it. The attachment of the upper larger stems to the trunk were all accompanied by a thickening all around the base of the stem on the trunk in an outward tapering from stem to trunk to a width tree or four times the thickness of stem (2 pictures of section of trunk). This feature would insure great resistance to splitting in ice storms by this tree.

BRIEF DESCRIPTION OF THE VIEWS OF THE DRAWING

The first sheet of drawing contains 4 photographs which show, in turn:

At the top left, a specimen of the claimed tree in its fourth season of growth. This photograph depicts the presentation of leaves of the canopy, comparative leaf size and leaf spacing along the forming central leader and scaffold branches.

The top right photograph depicts the same specimen, against a contrasting background, in dormancy. The placement and angle of lateral branches and the color of the bark in dormancy can be seen in the specimen. The development of a fairly strong, straight central leader can also be seen in this view, with the healing lesion, about in the center of the photograph, resulting from inoculation testing of the tree as described above.

The bottom left photograph is a close-up view showing color of young bark, the shape, color and orientation of the bark lenticels, branch attachment characteristics and the ascending angles of scaffold branches.

The bottom right photograph is a top view of two rooted cuttings taken from this tree, and shows the leaf orientation, margins and length to width ratio characteristic of the leaves of this tree.

The second sheet of drawing contains 4 photographs showing:

In the top left photo a close-up view of the developing trunk of a specimen in its fourth year of development showing the initial furrowing of the bark and the coloration of the older bark.

The top right photograph shows samara from the seed parent of the tree of this application reflecting the interspecific character of the seed parent.

The bottom left photograph depicts the top surface of a typical leaf of this tree and shows the color, the matt to semi-glabrous surface aspect, shape, symmetry of venation from plan view, the double serration of the leaf margin, and the short petiole characteristic of leaves of this tree. This view also shows the left half of the leaf blade being slightly lobed at the attachment end, and the slightly-sunken character of the leaf veins.

The bottom right photograph shows the same leaf in reversed position to show the underside characteristics. Color, lack of tomentum, matt surface texture and characteristic conspicuous protruding venation are clearly shown.

SPECIFIC CHARACTERISTICS SET FORTH IN COMPARISON

Stems:

*Length.*—I. Length of new growth to 4 years old 18 in. — 8½ ft.: Ulmus Wideleaf. I. Length of new growth to 4 years old 8 in. — 2 ft.: *Ulmus americana.*

*Attachment.*—I. Thickening of trunk around base of attached branch: Ulmus Wideleaf. I. Thickening not evident at base of branches: *Ulmus americana.*

Buds: I. Axillary buds found on all new growth. One half of axillary buds closest to stem accompanied by accessory buds: Ulmus Wideleaf. I. Axillary buds only found on new growth: *Ulmus americana.*

Leaves:

*Venation of leaves.*—I. Midrib and blade an inch above petiole measured by micrometer for thickness was 0.008 to 0.0085 inches: Ulmus Wideleaf. I. Midrib and blades an inch above petiole was 0.002 to 0.0022 inches in thickness: *Ulmus americana.*

*Duration of leaves.*—I. Leaves dropping a day or two after a killing frost with very little yellowness: Ulmus Wideleaf. I. Leaves turning yellow not dropping for a week or more: *Ulmus americana.*

*Leaf size.*—A. Thickness of blade by micrometer: I. Blade thickness between the veins 0.0042 to 0.0045 inches: Ulmus Wideleaf. I. Blade thickness between the veins 0.002 to 0.0022 inches: *Ulmus americana. B. Length and width of blade: I. Length of* 6–10 inches by a width of more than half the length: Ulmus Wideleaf. I. Length of 3–6 inches with width less than half the length: *Ulmus americana.*

*Base of blade.*—I. Base against the stem with its longest part, due to close petiole and large size of blade: Ulmus Wideleaf. I. Base not touching stem due to smaller size and longer petiole: *Ulmus americana.*

*Petiole length.*—I. Petiole less than ¼ inch to close: Ulmus Wideleaf. I. Petiole ½ inch or more in length: *Ulmus americana.*

BOTANICAL DESCRIPTION

A. Roots: Large branching roots ending in smaller ones and forming a mat of fibrous roots not only on the surface but reaching down as far as the subsoil and all about.

B. Stems: 1. Trunk caliber 18 inches above ground is 1 inch in diameter after 4 years of growth. 2. Top central stem of new growth 8½ feet in length. 3. Accompanied by five surrounding new growth, evenly spaced branches 2–6 feet in length. 4. Internodes of central 8½ foot stem numbered 48. 5. Base of new growth was covered with numerous finely branched smaller branches.

C. Bark: 1. New bark is smooth, dark reddish brown in color, lightly sprinkled with brownish gray lenticels. Becoming rougher with light fine gray lines appearing at the end of the growing season. 2. Maturing bark forms slightly wavy cracks of a light golden brown. Outer brown bark separating and flaking off to expose the light gray bark below. 3. Nodes are spaced 1–4 inches apart, being farthest apart on new growth of the thickest diameter nearest the trunk. The thickest being the central 8½ ft. stem that measured ⅝ inches in diameter near the base. Where the stem of new growth 2 feet or more in length is attached to the trunk, there are thickenings of the trunk to 4 times the diameter of stem width at trunk base, creating insurance against limb splitting (picture). 4. Pith continuous. 5. Scars. Stipule scars are present and reach to half way around the stem on each side of leaf scar.

Buds: 1. Buds are covered with dark brown colored scales, widest in the center, tapering lightly to the base and sharply to the tip. 2. Axillary buds were found on the new growth nodes of all branches. 3. Accessory buds were found on central new growth 8½ ft. stem and five top growth stems around it. Accompanying axillary buds were present for half the distance upward on their thickest diameter. 4. Bud size was ⅛ inch thick and ¼ inch long.

E. Leaves: 1. Venation is pinnate with large thick midrib and thinner lateral veins, glabrous, light green color. 2. Leaf arrangement alternate. 3. Simple leaf type. 4. Leaves deciduous, forming the first of Jun. and dropping near the middle of Oct., remaining dark green until a hard freeze, then falling within a day or two. 5. Blades are shaped elliptical, usually wider at the center than half the length. 6. Apex of the blade is acuminate. 7. Base of the blade is oblique, with longest side touching the stem. 8. Margin is double serrated. 9. Petiole is less than ¼ inch to close. 10. Surface of leaves is pubescent to glaborate. 11. Flowers and seed not on this young a tree. 12. Color according to Wilson Color Chart 1938. Upper surface of leaves were Paris green, page 58, No. 1 shade. Lower surface of leaves were Paris green, page 58, of a lighter shade. Branches are a gray green, page 55, No. 1 shade. Buds are a lighter gray green with brown. 13. Color of this tree closely resembles parent tree color. 14. This tree has proved hardy −20° in Wisconsin.

GENERAL OBSERVATIONS

Observations of leaves after dropping in dormant condition and becoming dry, and dried specimen leaves of 1992: Green attached leaves of *Ulmus americana* measured 0.0020 to 0.0022 inch in thickness. When dried they became 0.0008 to 0.0010 inch thick and remained relatively flat.

Ulmus 'Wideleaf' measured 0.0042 to 0.0045 inch thick when they were green and attached. When dried they became 0.0010 to 0.0012 inch in thickness and the retrorse curve that was their shape when green curled upward and the edges rolled into a ball one-half to one-third of the previous size.

I claim:

1. A new and distinct variety of Elm tree, substantially as described and illustrated.

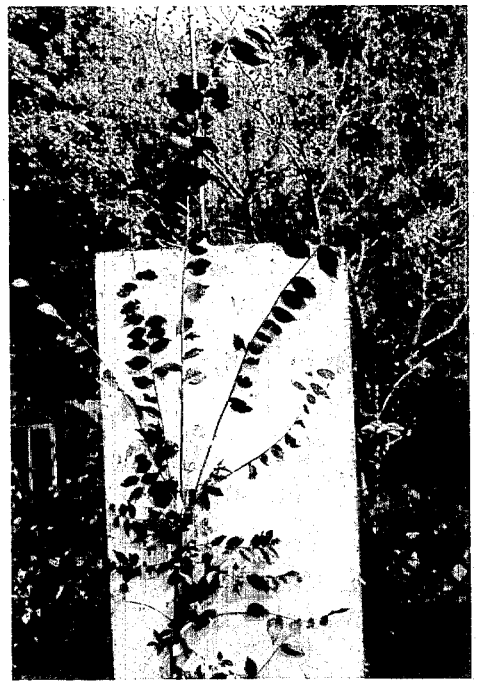
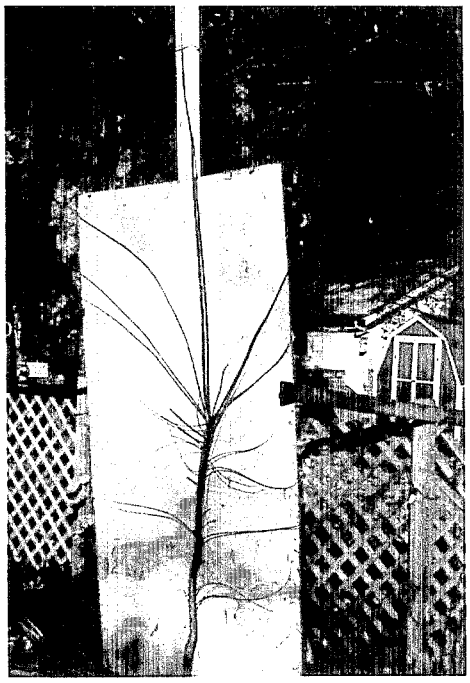
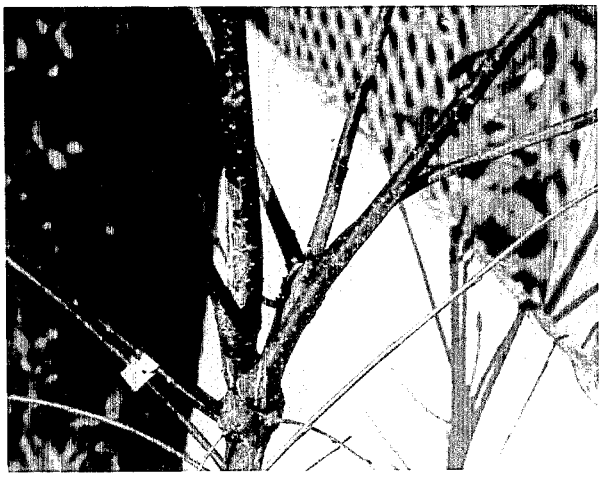
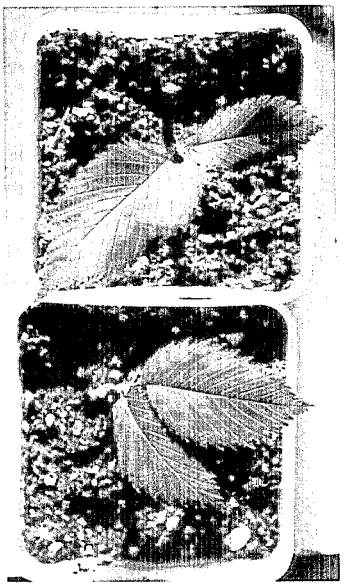

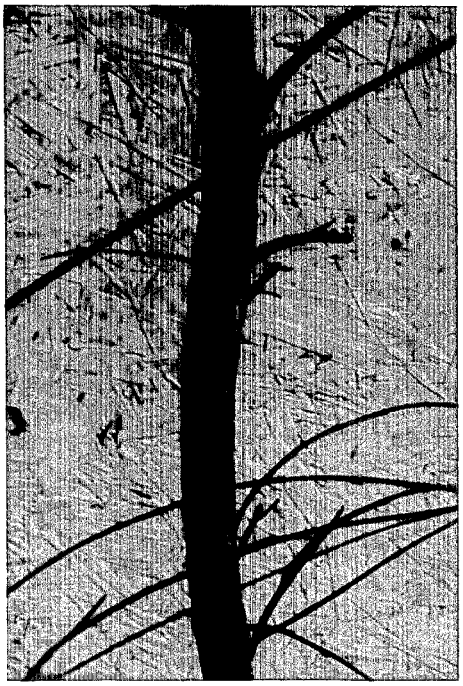
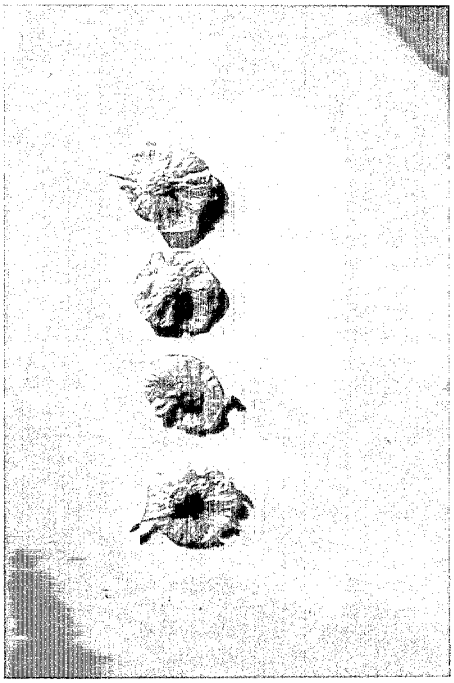
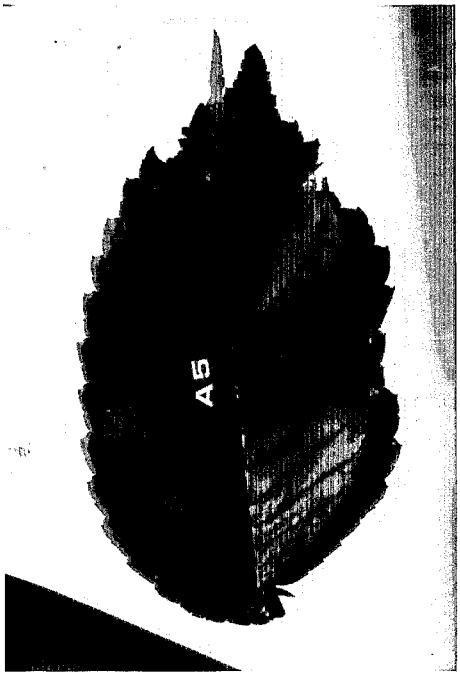
A5
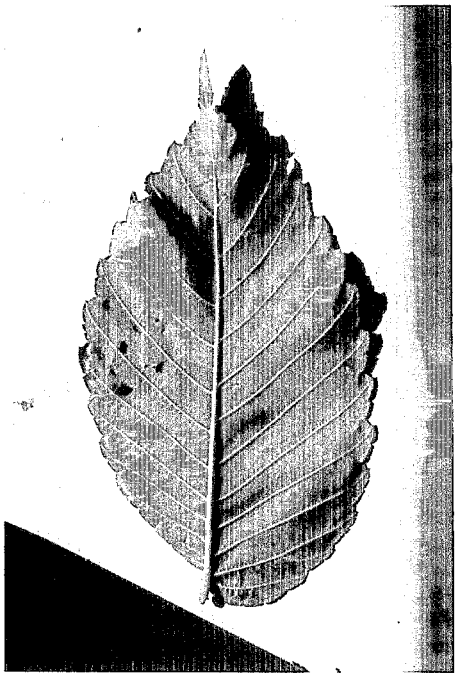

* * * * *